United States Patent [19]

Shimizu et al.

[11] Patent Number: 4,579,122

[45] Date of Patent: Apr. 1, 1986

[54] ULTRASONIC SCANNER

[75] Inventors: Wataru Shimizu; Jitsuo Toda, both of Tokyo; Teruhumi Akama, Ootawara; Youshichi Kikuchi, Tochigi, all of Japan

[73] Assignees: Kabushiki Gaisha SG, Kokubunji; Kabushiki Kaisha Toshiba, Kawasaki, both of Japan

[21] Appl. No.: 658,314

[22] Filed: Oct. 5, 1984

[30] Foreign Application Priority Data

Oct. 7, 1983 [JP] Japan ................. 58-186945

[51] Int. Cl.$^4$ ................................. A61B 10/00
[52] U.S. Cl. ........................... 128/660; 73/620
[58] Field of Search ................ 128/660, 661; 73/618–620

[56] References Cited

U.S. PATENT DOCUMENTS

| | | | |
|---|---|---|---|
| 3,927,661 | 12/1975 | Takemura | 128/660 |
| 4,106,492 | 8/1978 | Schuette et al. | 128/661 |
| 4,120,291 | 10/1978 | Paton et al. | 73/620 |
| 4,149,419 | 4/1979 | Connell, Jr. et al. | 128/660 X |
| 4,151,834 | 5/1979 | Sato et al. | 128/661 X |
| 4,215,585 | 8/1980 | Kunii et al. | 73/633 |
| 4,399,703 | 8/1983 | Matzuk | 128/660 X |
| 4,418,698 | 12/1983 | Dory | 128/660 |
| 4,421,118 | 12/1983 | Dow et al. | 128/660 |
| 4,424,813 | 1/1984 | Havlice et al. | 128/660 |
| 4,479,388 | 10/1983 | Matzuk | 128/660 X |

Primary Examiner—Kyle L. Howell
Assistant Examiner—Francis J. Jaworski

Attorney, Agent, or Firm—Finnegan, Henderson, Farabow, Garrett & Dunner

[57] ABSTRACT

The rotation of a motor is converted into a swinging movement of an ultrasonic transducer by a conversion mechanism. The relationship between a rotation angle $\theta$ of the motor and a swinging angle $\eta$ of the ultrasonic transducer can be expressed by $\eta = \tan^{-1}(\sin\theta)$. The rotation of the motor is detected by a rotation detector of a reluctance type having an eccentric rotor. A signal having a nonlinear relationship with respect to an actual rotation angle $\theta$ of the motor, which can be expressed by the following equation, is supplied to a motor driver from the rotation detector:

$$\theta_D = \theta + K \sin 2\theta.$$

A dummy rotation angular velocity $\omega_D$ which is a rate of change with respect to a time of a dummy rotation angle $\theta_D$ is obtained by the driver. The motor is servo-driven with reference to a deviation value between the dummy rotation angular velocity $\omega_D$ and a velocity setting value $\omega_M$. Therefore, the motor is rotated so that the rotation angle $\theta$ has the nonlinear relationship with respect to time t, as expressed in the following equation:

$$\theta = \omega_M t - K \sin 2\omega_M t.$$

A scanning velocity V of an ultrasonic beam is substantially constant.

11 Claims, 14 Drawing Figures

F I G. 6
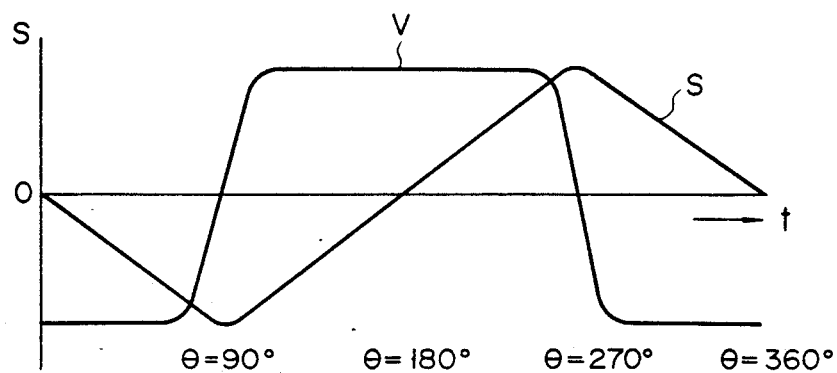
F I G. 7
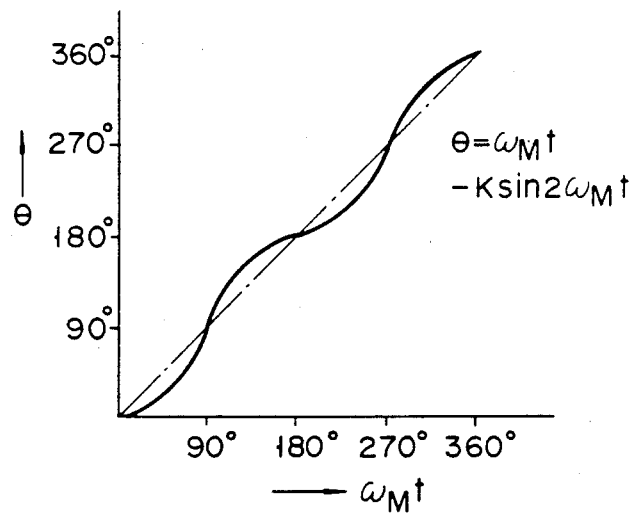

F I G. 13
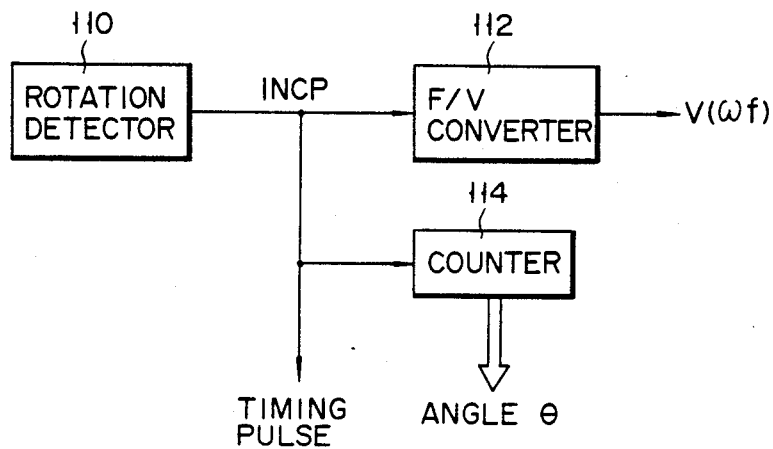
F I G. 14
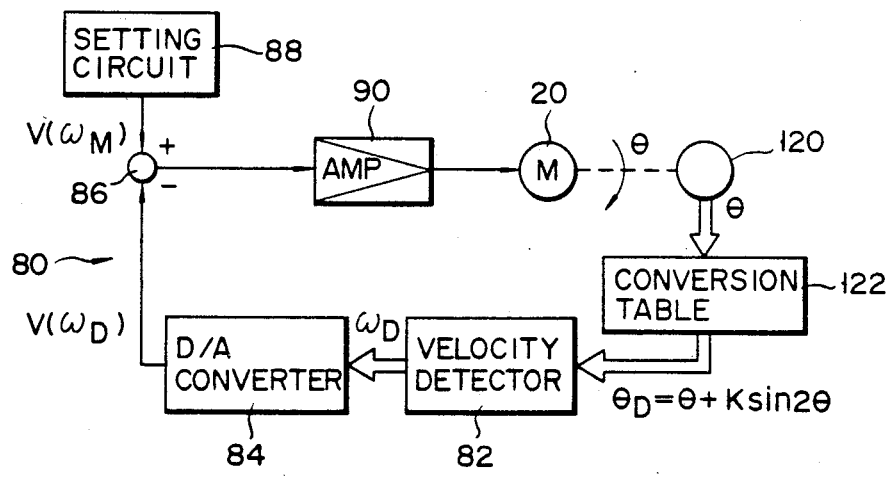

ULTRASONIC SCANNER

BACKGROUND OF THE INVENTION

The present invention relates to an ultrasonic scanner in which rotation of a motor is converted into a swinging movement of an ultrasonic transducer, thereby producing a scanning ultrasonic beam.

In an ultrasonic diagnostic apparatus, an ultrasonic transducer is supported to be swingable about an axis perpendicular to an ultrasonic beam irradiation direction. A disc is arranged on a rotating shaft of a motor. The rotation of the motor is converted by a link, which couples a peripheral portion of the disc and the transducer, into a swinging movement of, for example, an angle of about 90 degrees. When the motor is rotated once, the transducer reciprocates once to return to its initial position. Therefore, the motor is continuously rotated, thereby continuously operating a transducer. This mechanism is simple and inexpensive.

FIG. 1 shows the relationship between the rotation of a motor and the ultrasonic beam radiation direction of a transducer. When the rotating shaft 10 of a motor is rotated, a coupling point 12, which couples a peripheral portion of a disc and an arm, is rotated. In synchronism with this rotation, a transducer is swung about a swinging center 14, and an ultrasonic beam 16 is scanned at an angle of $\eta_o$. In this case, a scanning distance S of the ultrasonic beam 16 is in proportion to $\eta$, where $\eta$ is the swinging angle. Furthermore, when an angular velocity of the motor is given by $\omega$, a rotation angle by $\theta$ ($\theta = \omega t$), and a time by t, the scanning distance S of the ultrasonic beam 16 is in proportion to $\tan^{-1}(\sin \theta)$. Therefore, the scanning distance S of the ultrasonic beam 16 is changed in accordance with the rotation angle $\theta$ or time t, as shown by a curved line S in FIG. 2. Since a scanning velocity V is obtained by differentiating the scanning distance S, it is substantially in proportion to $\cos \theta$ and is indicated by a curved line V in FIG. 2.

In this manner, since the rotation angular velocity $\omega$ of the motor is constant, the scanning angle and the scanning distance of the ultrasonic beam 16 are changed at a velocity substantially in proportion to $\cos \theta$. The scanning velocity V becomes maximum at a center of a scanning stroke (S=0) and becomes zero at a stroke end. Since ultrasonic pulses are generated at predetermined intervals, respective intervals between positions to be subjected to ultrasonic diagnosis are increased at a scanning center and are decreased at a scanning end. However, data acquisition near a scanning center is most important for ultrasonic diagnosis. For this reason, a conventional ultrasonic scanner has a defect in that the number of diagnostic data at this important position is small. In order to increase the number of data at the scanning center, an irradiation interval of ultrasonic pulses may be shortened, but, in this case, a depth of view for ultrasonic diagnosis becomes undesirably shallow.

SUMMARY OF THE INVENTION

It is an object of the present invention to provide an ultrasonic scanner in which a scanning velocity is set to be constant or the scanning velocity at a scanning center is set to be slower than that at a scanning end, so that a plurality of ultrasonic data can be obtained at short measuring intervals near the scanning center and that accuracy and reliability of ultrasonic diagnosis is improved.

According to the present invention, there is provided an ultrasonic scanner in which ultrasonic beams scan an object to be examined at predetermined stroke and velocity characteristics. This ultrasonic scanner comprises a motor, an ultrasonic transducer for generating an ultrasonic beam, and a supporting means for swingably supporting the ultrasonic transducer around a swinging shaft. The ultrasonic transducer is swung, so that the ultrasonic beams scan the object to be examined at a predetermined stroke. A converting mechanism converts the rotation of a motor into a swinging movement of the ultrasonic transducer. A changing means is provided for changing the rotation velocity of the motor in accordance with its rotation angle. This changing means adjusts the rotation velocity of the motor, so that a scanning velocity of the ultrasonic beam, generated from the ultrasonic transducer and irradiating a center of a scanning stroke, is set to be equal to or slower than those irradiating portions other than the center of the scanning stroke.

According to the present invention, the motor is rotated at a inconsistant velocity so that the scanning velocity becomes constant. According to this, the ultrasonic transducer widely scans an object to be examined at a constant velocity throughout the scanning stroke. Since the ultrasonic transducer generates ultrasonic pulses having a predetermined interval, a density of the ultrasonic beams becomes constant throughout the scanning stroke. A scanning velocity at a scanning center is set to be slower than that at a scanning end, thereby obtaining a number of ultrasonic data having short measuring intervals near the scanning center. Therefore, reliability and accuracy of ultrasonic diagnosis can be improved, and furthermore, the structure of the scanner is simple and has a relatively low manufacturing cost.

BRIEF DESCRIPTION OF THE DRAWINGS

FIG. 6 is a graph showing the relationship between a scanning distance S and a scanning velocity V when the scanning distance S is changed at a constant rate;

FIG. 7 is a graph showing the relationship between a rotation angle $\theta$ of the motor and time t when the scanning distance S is changed at a constant rate;

FIG. 13 is a block diagram of a rotation detector of an incremental pulse type; and FIG. 14 is a block diagram of a rotation detector connected to a conversion table.

DETAILED DESCRIPTION OF THE PREFERRED EMBODIMENT

Figure 1:
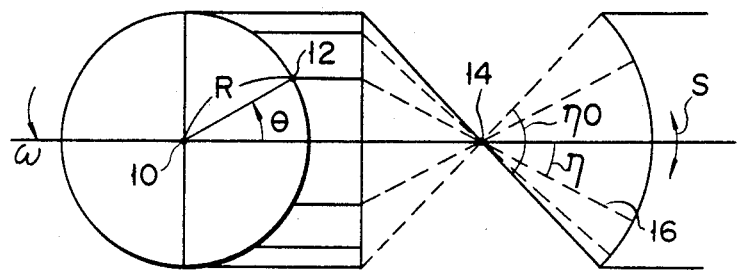
FIG. 1 is a representation showing a stroke of an input rotational movement and an output stroke movement in a mechanism for converting a rotation of a motor into a swing movement of a transducer.
Figure 2:
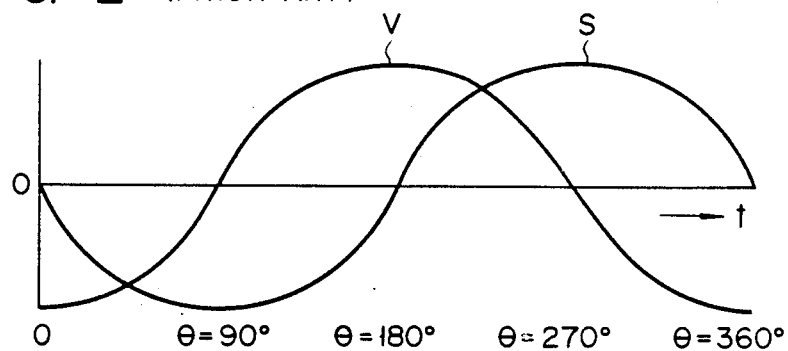
FIG. 2 is a graph showing the relationship between shifting amount of the output stroke movement and a velocity when the motor is rotated at a constant velocity.
Figure 3:
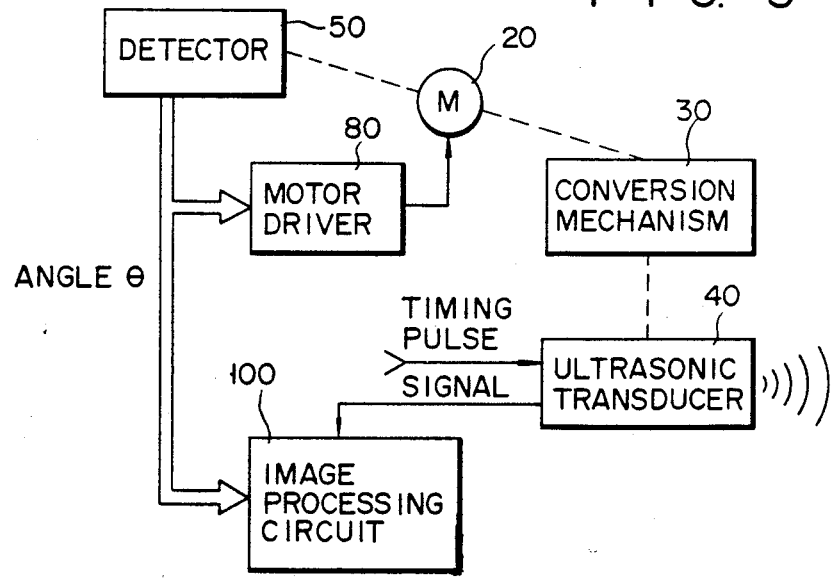
FIG. 3 is a block diagram showing an overall structure of an ultrasonic scanner according to an embodiment of the present invention.

FIG. 3 shows a block diagram showing the overall configuration of an ultrasonic scanner according to an embodiment of the present invention. A rotational movement of a motor 20 is converted into a swinging movement of an ultrasonic transducer 40 by a conversion mechanism 30. A rotation detector 50 is coupled to the motor 20, and an output thereof is supplied to a motor driver 80 which controls a rotation velocity of the motor 20. An output of the ultrasonic transducer 40 is supplied to an image processing device 100, and data of a rotational position of the motor 20 is detected by a rotation detector 50 is also supplied thereto. Pulse signals are supplied to the ultrasonic transducer 40 at a predetermined time from an ultrasonic generator (not shown). The ultrasonic transducer 40 thus generates ultrasonic pulses.

Figure 4:
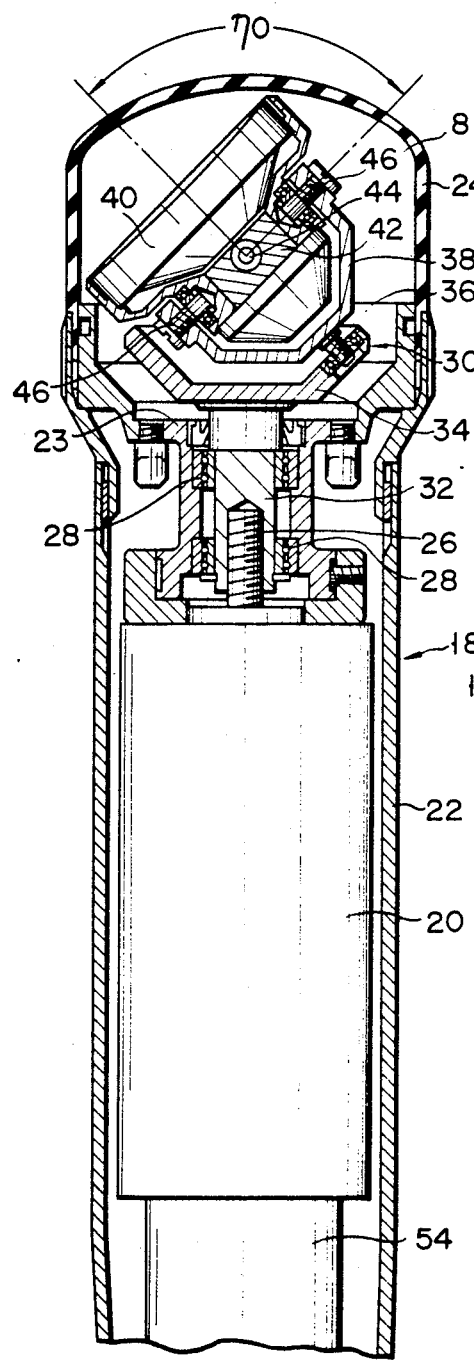
FIGS. 4 and 5 are respectively sectional views of an ultrasonic probe.
Figure 5:
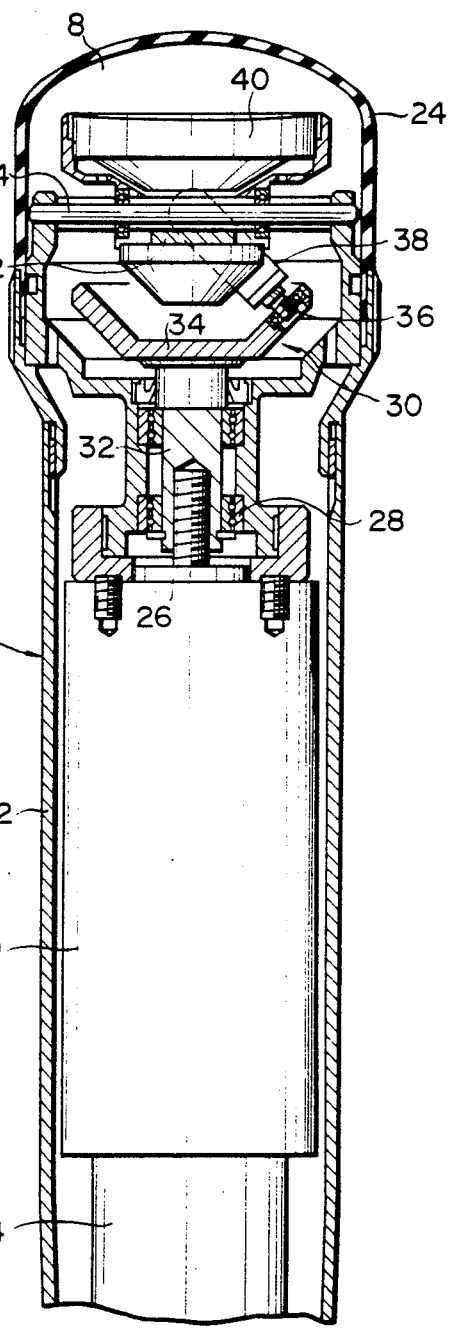

The conversion mechanism 30 of an ultrasonic probe 18 will now be described with reference to FIGS. 4 and 5. FIGS. 4 and 5 are sectional views along planes perpendicular to each other. The motor 20 is stored in a case 22 of the probe 18. A bag 24 of material having a low absorbency of ultrasonic beams is mounted at the top end of the case 22. This bag 24 is separated from the main portion of the case 22 by a partition wall 23. A rotating shaft 32 of the conversion mechanism 30 is coaxially arranged on a rotating shaft 26 of the motor 20. The rotating shaft 32 extends through the wall 23 and is rotatably supported by bearings 28. A dish-shaped rotation member 34 is coaxially fixed at the top end of the rotating shaft 32.

A swinging shaft 44 is fixed in the case 22 so that the axial direction thereof is perpendicular to the rotation shaft 26. The ultrasonic transducer 40 is fixed to a supporting member 42. The supporting member 42 is rotatably supported by the swinging shaft 44. Thus, the ultrasonic transducer 40 can swing about the swinging shaft 44. An arm 38 is disposed between the rotation member 34 and the supporting member 42. The arm 38 is rotatably coupled to the supporting member 42 through a pivot shaft 46 and is rotatably coupled to the rotation member 34 through a pivot shaft 36. Central axes of the swinging shaft 44 and the pivot shafts 36 and 46 are perpendicular to each other. With this arrangement, when the rotation member 34 is rotated once, the ultrasonic transducer 40 is swung through an angle of $\eta_o$ about the swinging shaft 44, and then returned to its initial position. Therefore, when the motor 20 is rotated once, an ultrasonic beam generated from the transducer 40 reciprocally scans once at the angle $\eta_o$.

In the conversion mechanism 30 having such a structure, if an angular rotation velocity $\omega$ of the motor 20 is constant, a scanning distance S is substantially in proportion to sin $\theta$, and a scanning velocity V is substantially in proportion to cos $\theta$. In order to maintain a constant scanning velocity V according to a scanning stroke (i.e., a rotation angle $\theta$ of the motor 20 is 0, 180, 360 degrees, . . . at a scanning center), the rotation angular velocity $\omega$ of the motor 20 must be changed in accordance with the rotation angle $\theta$. In other words, the swinging angle $\eta$ must be changed with respect to time t in accordance with a triangular wave, as indicated by a curved line S in FIG. 6.

The present inventors confirmed that the rotation of the motor 20 was changed at a period having twice a constant angular rotation velocity $\omega_M$ of the motor 20 (i.e., an angular velocity component $2\omega_M$, where $\omega_M$ is constant), thereby obtaining an inconstant rotation of the motor 20.

This can be explained as follows. In order to simplify this explanation, assume that a radius of rotation of the pivot shaft 36 (i.e., the distance between the pivot shaft 36 and the center of the rotating shaft 26) is equal to the distance between the rotation center of the pivot shaft 36 and the swinging shaft 44. When the ultrasonic beam is directed toward the scanning center (i.e., the scanning direction coincides with the direction of rotation of the rotating shaft of the motor 20), the swinging angle is assumed to be zero. When the rotating shaft 26 is rotated at an angle $\theta$, the swinging angle is given to be $\eta$. In this case, the relation between $\theta$ and $\eta$ is given as in equation (1):

$$\tan \eta = \sin \theta (\text{or}, \eta = \tan^{-1}(\sin \theta)) \tag{1}$$

In this case, the rotation angle $\theta$ is periodically changed by an angular velocity component $2\omega_M$ (i.e., twice the steady state angular velocity $\omega_M$) from the linear relationship between $\theta$ and t, as expressed by equation (2):

$$\theta = \omega_M t - K \sin 2\omega_M t \tag{2}$$

where K is a constant which determines the value of the angular velocity component. Equation (2) can be expressed as a graph, as shown in FIG. 7. In FIG. 7, the one-dotted chain line indicates $\theta = \omega_M t$, and the solid line indicates equation (2). As is apparent from this graph, in order to change the scanning distance S at a constant rate, the rotation angle $\theta$ of the motor 20 is periodically shifted with respect to time t from a straight line of $\theta = \omega_M t$. The angular velocity of the motor 20 is changed during two periods, while the motor 20 is rotated once.

Equation (2) means that the angular velocity $\omega (= \theta/t)$ of the motor 20 is changed with respect to time in accordance with the following equation (3):

$$\omega = \omega_M - (K/t) \sin 2\omega_M t \tag{3}$$

When equation (2) substitutes for equation (1), $\eta$ can be expressed as follows:

$$\eta = \tan^{-1}\{\sin (\omega_M t - K \sin 2\omega_M t)\} \tag{4}$$

From equation (4), $\eta$ can be expressed by the following approximation:

$$\eta = a \sin \omega_M t + b \sin 3 \omega_M t + c \sin 5\omega_M t + d \sin 7\omega_M t \tag{5},$$

where coefficients a, b, c, and d are constants determined in accordance with the value of the coefficient K.

In order to change the scanning distance S at a constant rate, it must be changed with respect to time t in accordance with a substantially triangular wave, as shown in FIG. 6. In this case, the swinging angle $\eta$ changes in accordance with a Fourier expansion as follows:

$$\eta = \sin \omega_M t - (1/9) \sin 3\omega_M t + (1/25) \sin 5\omega_M t \quad (6).$$

If the coefficient K of equation (2) is properly set, the coefficients a, b, c and d of equation (5) can be set at values close to ideal values. In the case wherein the coefficient K is set in this manner, when $\theta$ is changed with respect to time t as expressed in equation (2), the scanning distance S can be changed at a constant rate.

In this embodiment, the motor 20 is rotated at an inconsistent velocity by the rotation detector 50 and the motor driver 80. The rotation detector 50 will be described with reference to FIG. 8. The rotation detector 50 comprises an encoder 54 and a sensor 52, which converts changes in the rotation angle into changes in reluctance. This rotation detector of the reluctance type has been reported in Japanese Patent Disclosure No. 82-70406, and so will be only briefly described below. The sensor 52 comprises a stator 56, which is coaxially disposed to the rotating shaft 26 of the motor 20, and an eccentric rotor 60 fixed to the rotating shaft 26. Four magnetic poles 56a, 56b, 56c and 56d are arranged in the stator 56 to be separated by a predetermined distance. A primary coil 58a is wound around the magnetic poles 56a and 56c, and one end of the coil 58a is grounded, and the other end is coupled to a sine wave generating terminal of a current generating circuit 62. A primary coil 58b is wound around the magnetic poles 56b and 56d, and one end of the coil 58b is grounded, and the other end is coupled to a cosine wave generating terminal of the current generating circuit 62. A secondary coil 58c is wound around the magnetic poles 56a, 56b, 56c and 56d. One end of the coil 58c is grounded, and the other end is coupled to a zero crossing detector 64. A counter 66 is coupled to the generating circuit 62 and the detector 64. A clock 68 is coupled to the counter 66. Clock pulses generated from the clock 68 are supplied to the counter 66 at a predetermined period. The counter 66 starts the counting operation in response to a start signal from the generating circuit 62 and stops it in response to a stop signal from the detector 64. A count value of the counter 66 is latched in a latch 70.

In the rotation detector 50 having such a configuration, the primary coils 58a and 58b are excited by the current generating circuit 62 at currents $\sin \omega_M t$ and $\cos \omega_M t$, respectively. Then, a magnetic path which couples the magnetic poles 56a and 56c and a magnetic path which couples the magnetic poles 56b and 56d are respectively formed between the stator 56 and the rotor 60. Since the rotor 60 has an eccentric structure, a gap between the stator 56 and the rotor 60 is continuously changed about the respective magnetic paths by the rotation of the rotating shaft 26 of the motor 20. Changes in the gap are converted into changes in reluctance, thereby changing an excitation voltage E of the secondary coil 58c. If the excitation currents $\sin \omega_M t$ and $\cos \omega_M t$ have the same amplitude, the secondary coil excitation voltage E can be expressed as follows:

$$E = \sin(\omega_M t - \theta) \quad (7).$$

An output voltage of the secondary coil has a phase angle equal to the rotation angle $\theta$ of the rotor 60.

The output voltage E of the secondary coil 58c is supplied to the zero crossing detector 64. When the output voltage E becomes zero, the detector 64 supplies the stop signal to the counter 66. On the other hand, when the excitation currents $\sin \omega_M t$ and $\cos \omega_M t$ respectively become zero, the generating circuit 62 supplies the start signal to the counter 66. When the start signal is supplied to the counter 66, the counter 66 clears the previous count and resumes the counting operation of the clock pulses from the clock 68. When the stop signal is supplied to the counter 66, the counter 66 transmits this count to the latch 70. The output of the detector 64 can serve as a scanning start timing pulse of the ultrasonic transducer 40. The output signal which is generated when the detector 64 detects a zero crossing is also supplied to the transducer 40. When the transducer 40 receives the stop signal, it can start the scanning operation.

As described above, amplitudes of the reference AC currents $\sin \omega_M t$ and $\cos \omega_M t$ supplied to the sensor 52 are set to be the same, so that a signal which changes linearly with respect to the rotation angle $\theta$ of the motor 20 can be generated. According to this advantage, this detector has been conventionally used for detecting a rotational position of a rotor (rotation angle $\theta$), as reported in Japanese Patent Disclosure No. 82-70406. However, in this embodiment, amplitudes of the excitation AC currents $\sin \omega_M t$ and $\cos \omega_M t$ are different from each other, and a dummy rotation angle $\theta_D$ which is shifted by $\Delta\theta$ is thereby generated from the rotation detector 50 with respect to the rotation angle $\theta$. $\Delta\theta$ is in proportion to $\sin 2\theta$ as follows:

$$\theta_D = \theta + \Delta\theta = \theta + P \sin 2\theta \quad (8).$$

The absolute value of a coefficient P becomes large in accordance with an increase in the difference between respective amplitudes of the excitation AC currents $\sin \omega_M t$ and $\cos \omega_M t$. For example, when the ratio of difference in amplitudes is 1%, 2% and 3%, they respectively correspond to angles of about 0.3 degrees, 0.5 degrees and 0.9 degrees. Therefore, when the difference between amplitudes of the currents $\sin \omega_M t$ and $\cos \omega_M t$ is properly set, the coefficient P can coincide with the coefficient K for changing the scanning distance S at a constant velocity.

Figure 9:
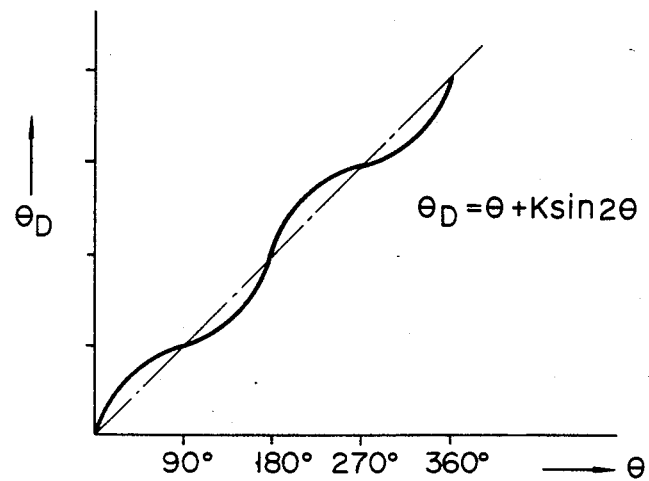
FIG. 9 is a graph showing the relationship between an output of the rotation detector $\theta_D$ and a rotation angle $\theta$ of the motor.

In this case, the dummy rotation angle $\theta_D$, generated from the rotation detector 50, is changed with respect to time t, as shown in FIG. 9, and can be expressed as follows:

$$\theta_D = \theta + K \sin 2\theta \quad (9).$$

Figure 10:
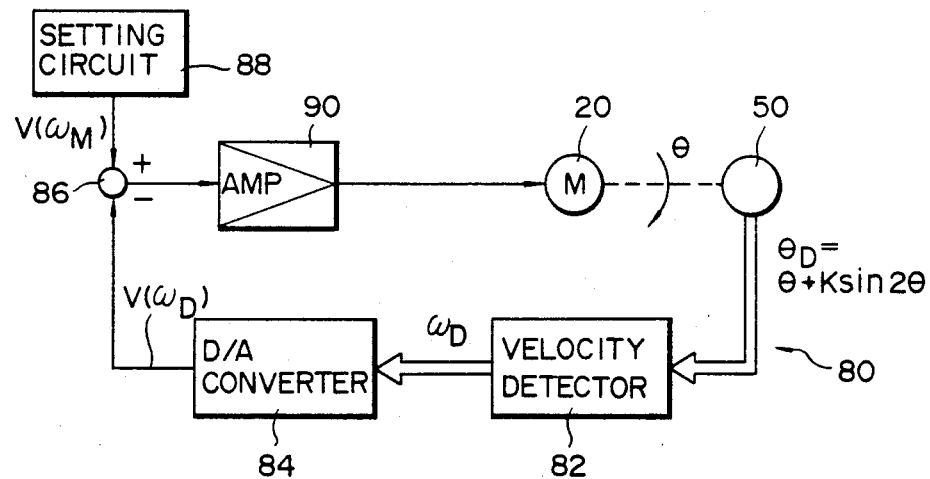
FIG. 10 is a block diagram of a motor driver.

This dummy rotation angle $\theta_D$ is supplied to the motor driver 80, as shown in FIG. 10. A velocity detector 82 of the motor driver 80 calculates a rate of change (differentiated value) of the dummy rotation angle $\theta_D$ from the rotation detector 50 with respect to a predetermined period of time, thereby obtaining a dummy rotation velocity $\omega_D$. This dummy rotation velocity $\omega_D$ is converted into an analog signal $V(\omega_D)$ by a D/A converter 84, and the signal $V(\omega_D)$ is supplied to a deviation detector 86. The deviation detector 86 also receives an angular velocity setting signal $V(\omega_M)$ from an angular velocity setting circuit 88, and a deviation value between $V(\omega_M)$ and $V(\omega_D)$ is obtained by the deviation detector 86. This deviation value is supplied to a servo amplifier 90 to be amplified and is used for driving the motor 20.

Figure 11:
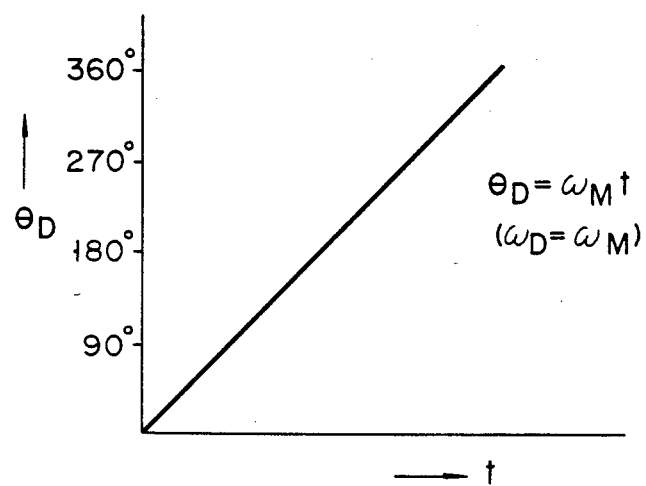
FIG. 11 is a graph showing the relationship between an output of the rotation detector $\theta_D$ and time t, when $\omega_M = \omega_D$.
Figure 12:
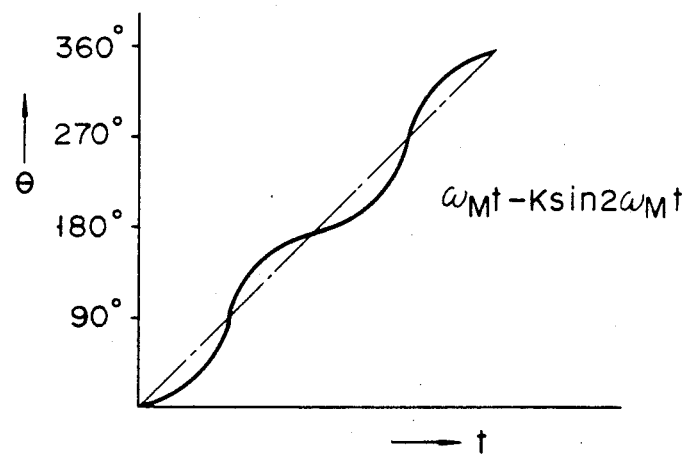
FIG. 12 is a graph showing the relationship between a rotation angle $\theta$ of the motor and time t when $\omega_M = \omega_D$.

In a servo loop, the rotation of the motor 20 is controlled to establish $V(\omega_M) = V(\omega_D)$. However, since the dummy angular velocity $\omega_D$ is obtained with reference to the relation of $\theta_D = \theta + \sin 2\theta$, the motor 20 is rotated at an inconstant velocity when the servo loop is stabilized. If the detected value $\theta_D$ of the rotation detector 50 were equal to $\omega_M t$ ($\omega_M = \omega_D$), the motor 20 would be rotated at a constant velocity as shown in FIG. 11. However, as described above, the rotation detector 50 supplies the dummy rotation angle $\theta_D$, given by equation (9) above, to the motor driver 80. For this reason, the motor 20 has an inconstant rotation, as expressed by equation (2) and as shown in FIG. 12. Then, the scanning distance S of the ultrasonic transducer 40 is changed at a constant rate, and the scanning velocity V becomes constant.

As shown in FIG. 3, the ultrasonic transducer 40 receives scanning timing pulses from the clock 68 at a predetermined interval, and an ultrasonic beam is generated in accordance therewith at any position. Since the scanning velocity V is constant within an overall range of the scanning stroke about the scanning center, ultrasonic pulses, generated in accordance with constant scanning timing pulses, scan an object to be examined at predetermined intervals.

An echo pulse reflected in an object to be examined such as a patient is detected by the transducer 40, and a reception signal from the transducer 40 is supplied to a known image processing circuit 100. The image processing circuit 100 processes this reception signal and changes it into proper data. Data of the rotation angle $\theta$ from the rotation detector 50 is also supplied to the image processing circuit 100, and the ultrasonic data is corresponded to the scanning distance S, thereby displaying a slice image at its scanning line. A digital scan converter can be provided to display the ultrasonic data on a television image. In the digital scan converter, these ultrasonic data are stored in a memory in correspondence with the respective scanning lines. These data are read out in accordacne with a television format and are displayed on a CRT.

The operation of the ultrasonic scanner having the above configuration will now be described. The motor 20 is rotated by the motor driver 80. The rotation of the motor 20 is converted into a swinging movement of the ultrasonic transducer 40 by the converting mechanism 30. The rotation of the motor 20 is detected by the rotation detector 50. The dummy rotation angle $\theta_D$, which is shifted from the actual motor rotation angle $\theta$ at a period $\frac{1}{2}$ the rotation period of the motor 20, is generated by the rotation detector 50. The dummy rotation angular velocity $\omega_D$, which is a rate of change of the dummy rotation angle $\theta_D$, is obtained by the motor driver 80. Then, the motor 20 is driven by the servo amplifier 90 with reference to a deviation value between the dummy rotation angular velocity $\omega_D$ and the velocity setting value $\omega_M$ (which is constant). The motor 20 is rotated at an inconstant velocity which periodically changes at twice an angular velocity component with respect to time t, as shown in FIG. 7. The ultrasonic beam scans an object to be examined at the constant scanning velocity V. Ultrasonic pulses are generated from the ultrasonic transducer 40, and ultrasonic data having a higher density than in the conventional case and a constant scanning interval can be obtained at the scanning center.

In order to obtain a nonlinear output of the rotation detector 50, as shown in FIG. 9, amplitudes of the currents sin $\omega_M t$ and cos $\omega_M t$ are not always different, from each other as described above, but a phase difference between two currents can be started to change from 90 degrees.

Figure 8:
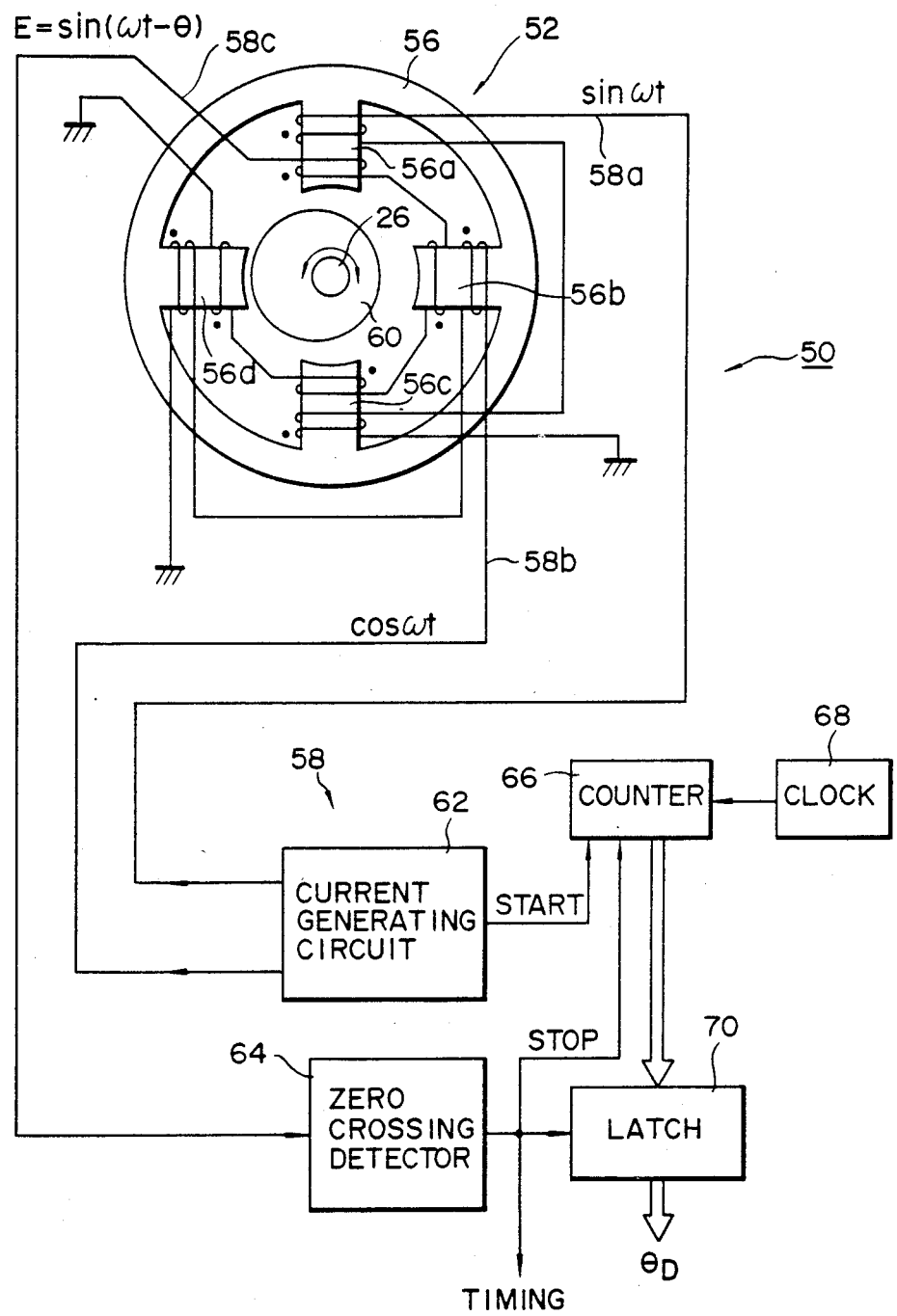
FIG. 8 is a block diagram of a rotation detector.

A rotation detector having nonlinear detection characteristics is not limited to one of a variable reluctance type, as shown in FIG. 8, but can be a phase shift sensor of a variable magnetic coupling type such as a resolver.

A rotation detector of an incremental pulse generating type can also be used as the rotation detector. A rotation detector 110 shown in FIG. 13 is an incremental rotary encoder, which generates pulses with predetermined nonlinear characteristics (inconstant interval pitch). An output pulse INCP from the detector 110 is supplied to a frequency/voltage converter 112 so as to obtain an analog velocity detection signal $V(\omega_D)$. The signal $V(\omega_D)$ is supplied to the deviation detector 86 of FIG. 10. The output pulse INCP is supplied to the ultrasonic transducer 40 as an operation timing pulse. The pulse INCP is counted by a counter 114, thereby obtaining data on the rotation angle of the motor 20. This data is supplied to the image processing circuit 100 (FIG. 4).

In this case, when the motor 20 is rotated at a desired inconsistant velocity, as shown in FIG. 7, a pulse generating pattern is nonlinear with respect to the actual rotation angle $\theta$, so a generating time interval of the pulse INCP becomes constant. Therefore, the pulse INCP can serve as a clock pulse having a constant time interval. Furthermore, a count value of the counter 114 preferably corresponds to the scanning distance S of the ultrasonic transducer 40 within a range in which the ultrasonic transducer 40 scans at substantially constant velocity.

When the rotation detectors 50 (FIG. 8) and 110 (FIG. 13) are used, the detection data corresponds substantially linearly to the scanning distance S of the ultrasonic transducer 40. Therefore, the detection data of the detector 50 and 110 can be used as the scanning distance S in the image processing circuit 100.

However, in the present invention, the rotation detector is not limited to one having the above nonlinear detection characteristics, but may have linear detection characteristics. In this case, an inconstant motor velocity function corresponding to a detection value of a rotation angle of the motor is read out from a table and can be used to control the motor.

As shown in FIG. 14, a rotation detector 120 generates digital data linearly corresponding to the actual rotation angle $\theta$ of the motor 20. This data is supplied to a conversion table 122, thereby reading out $\theta_D$ expressed by equation (9). $\theta_D$ is supplied to the velocity detector 82 from the conversion table 122. The motor driver 80 performs the same operation as shown in FIG. 10. Therefore, the same reference numerals as in FIG. 10 denote the same parts in FIG. 14, and a detailed description of the motor driver 80 is omitted. In this embodiment, data having linear characteristics with respect to the rotation of the motor is generated from the rotation detector 120. Then, the data is converted into nonlinear data with respect to the rotation of the motor by the conversion table 122, and the dummy rotation angle $\theta_D$ is supplied to the velocity detector 82.

What is claimed is:

1. An ultrasonic scanner in which an ultrasonic beams scans an object to be examined through a predetermined scanning stroke having a central region and two opposite end points, the scanner comprising:

a unidirectional rotary motor having an output shaft, said motor in operation continuously rotating in one direction;

an ultrasonic transducer for generating an ultrasonic beam;

supporting means, including a transducer oscillating shaft extending in a direction substantially perpendicular to the output shaft of said motor, for supporting said ultrasonic transducer in such a manner that said transducer can be oscillated around said transducer oscillating shaft and through it predetermined scanning stroke;

coupling means for coupling said output shaft of said motor with the transducer oscillating shaft and converting the continuous unidirectional rotation of the output shaft into an oscillating motion of the transducer;

rotation angle detection means coupled with said motor for detecting the actual rotation angle of the output shaft of the motor and producing a nonlinear control signal which is a function of twice the detected actual rotation angle of the motor; and changing means, coupled with said rotation angle detection means and said motor, for changing the velocity of the output shaft of said motor in response to said control signal in a manner that causes the transducer to oscillate at a uniform velocity at least through the central region of the scanning stroke.

2. An ultrasonic scanner according to claim 1, wherein said rotation angle detection means generates a signal which is shifted from the actual rotation angle $\theta$ and corresponds to a dummy rotation angle $\theta_D$ expressed by the following equation:

$$\theta_D = \theta + K \sin 2\theta$$

where K is a constant.

3. An ultrasonic scanner according to claim 2, wherein said rotation angle detecting means includes a sensor and an encoder, said sensor including a ring-shaped stator, an eccentric rotor which is coupled to said motor and is concentrically provided in a stator, four magnetic poles arranged in said stator at equal intervals, a pair of primary coils which are wound around respective pairs of magnetic poles which are opposed to have said rotor therebetween, and a secondary coil which is wound around said four magnetic poles, and said encoder including a current generating circuit which excites said primary coils by alternate current signals respectively having different phases and amplitudes, and phase shift detecting means for detecting a phase shift amount of a secondary coil excitation voltage having a phase which is shifted in correspondence with a rotation angle of said rotor by a change in a reluctance or magnetic coupling upon rotation of said rotor.

4. An ultrasonic scanner according to claim 3, wherein said phase shift detecting means comprises a zero crossing detecting circuit for detecting a zero crossing of the secondary coil excitation voltage, and a counter to which a start signal is supplied when a generating circuit generates an alternate current signal and a stop signal is supplied from said zero crossing detecting circuit which said zero crossing detecting circuit detects a zero crossing, said counter starting a counting operation in response to the start signal and stopping the counting operation in response to the stop signal, whereby a phase shift amount is obtained by a count of said counter.

5. An ultrasonic scanner according to claim 4, wherein said changing means includes a motor driver including a velocity detecting circuit, to which a dummy rotation angle $\theta_D$ is supplied from said rotation angle detection means, for obtaining a dummy rotation angular velocity $w_D$ which is a rate of change with respect to a time of $\theta_D$, a digital/analog converter for converting the dummy rotation angular velocity $w_D$ into an analog signal $V(w_D)$, a setting unit for setting a velocity setting signal $V(w_M)$, a deviation detector, to which the analog signal $V(w_M)$ and the velocity setting signal $V(w_D)$ are supplied from said setting unit and said digital/analog converter, respectively, for detecting a deviation value between the two signals $V(w_D)$ and $V(w_M)$, and a servo amplifier which rotates said motor by an output from said deviation detector.

6. An ultrasonic scanner according to claim 2, wherein said rotation angle detecting means generates incremental pulses at a nonlinear interval with respect to the rotation angle of said motor; and said changing means includes a motor driver including a frequency/voltage converter for requency/voltage-converting the incremental pulses of said rotation angle detection means into an analog signal of a rotation angular velocity $V(w_D)$ of said motor, a setting unit for setting a velocity setting signal $V(w_M)$, a deviation detector to which the analog signal $V(w_M)$ and the velocity setting signal $V(w_D)$ are supplied from said setting unit and said frequency/voltage converter, respectively, for detecting a deviation value between the two signals $V(w_D)$ and $V(w_M)$, and a servo amplifier which rotates said motor by an output from said deviation detector.

7. An ultrasonic scanner according to claim 2, wherein said rotation detecting means comprises a rotation detector for generating a linear signal with respect to the rotation angle $\theta$ of said motor, and a conversion table for generating a nonlinear signal $\theta_D$ with respect to a signal $\theta$ of said rotation detector, which is expressed as follows:

$$\theta_D = \theta + K \sin 3\theta$$

8. An ultrasonic scanner according to claim 2, wherein said supporting means includes a supporting member, which is swingable around said transducer oscillating shaft, for supporting said ultrasonic transducer, said supporting member having first and second pivot shafts spaced apart in a direction perpendicular to said transducer oscillating shaft, respectively, and said coupling means includes, a rotation member fixed to said rotating shaft of said motor, said rotation member having a third pivot shaft spaced outside the axis of said rotating shaft of said motor, and said supporting member and said rotation member being coupled through said first, second and third pivot shafts in a manner so that the relationship between the rotation angle $\theta$ of said motor and the swinging angle $\eta$ of said ultrasonic transducer is expressed by the following equation:

$$\eta = \tan^{-1}(\sin \theta).$$

9. An ultrasonic scanner according to claim 8, wherein the swinging angle $\eta$ can be expressed by an equation approximate to a Fourier expansion.

10. The ultrasonic scanner of claim 1 wherein said changing means causes said motor to constantly change velocity throughout its operation and repeat a predetermined velocity change pattern two times for each complete rotation of the motor.

11. The ultrasonic scanner of claim 1 wherein said changing means causes said transducer to oscillate at a uniform velocity throughout the predetermined scanning stroke.

* * * * *